United States Patent [19]

Harding et al.

[11] Patent Number: 5,538,426

[45] Date of Patent: Jul. 23, 1996

[54] METHOD OF FORMING A DENTAL PROSTHESIS FOR MOUNTING IN AN IMPLANT, A METHOD OF FORMING A DENTAL MODEL FOR USE THEREIN, A DENTAL FORMATION MOUNTING ARRANGEMENT

[75] Inventors: Stewart P. Harding, Les Rosiers, Braye Road Vale, Guernsey, Channel Islands; George B. Asher, 6 Chestnut Close, Blackwater, United Kingdom

[73] Assignees: Stewart Peter Harding, Channel Islands; George Brian Asher, Surrey, both of United Kingdom

[21] Appl. No.: 46,731

[22] Filed: Apr. 16, 1993

[30] Foreign Application Priority Data

Apr. 16, 1992 [GB] United Kingdom ............ 9208442

[51] Int. Cl.⁶ ............ A61C 13/12; A61C 13/225; A61C 8/00; A61C 9/00
[52] U.S. Cl. ............ 433/172; 433/173; 433/214
[58] Field of Search .................. 433/172, 173, 433/174, 214, 213

[56] References Cited

U.S. PATENT DOCUMENTS

| | | |
|---|---|---|
| 4,708,654 | 11/1987 | Branemark . |
| 4,854,872 | 8/1989 | Detsch ............ 433/173 |
| 4,907,969 | 3/1990 | Ward ............ 433/173 |
| 4,955,811 | 9/1990 | Lazzara et al. ............ 433/213 X |
| 5,055,047 | 10/1991 | Names . |
| 5,071,351 | 12/1991 | Green, Jr. et al. ............ 433/173 |
| 5,104,318 | 4/1992 | Piche et al. ............ 433/173 X |
| 5,106,300 | 4/1992 | Voitik ............ 433/173 |
| 5,108,288 | 4/1992 | Perry ............ 433/173 |
| 5,135,395 | 8/1992 | Marlin ............ 453/174 |
| 5,152,687 | 10/1992 | Amino ............ 433/173 |
| 5,195,891 | 3/1993 | Sulc ............ 433/173 |
| 5,199,873 | 4/1993 | Schulte et al. ............ 433/173 X |
| 5,213,502 | 5/1993 | Daftary ............ 433/214 X |
| 5,234,339 | 8/1993 | Grigereit ............ 433/172 |
| 5,259,759 | 11/1993 | Jorneus et al. ............ 433/173 |

FOREIGN PATENT DOCUMENTS

| | | |
|---|---|---|
| 0439441A1 | 7/1991 | European Pat. Off. . |
| 1463860 | 11/1966 | France . |
| 3110694A1 | 9/1982 | Germany . |
| WP88/03007 | 5/1988 | WIPO . |

OTHER PUBLICATIONS

"Prosthodontic Procedures", by George A. Zarb and Tomas Jansson in "Tissue–Integrated Prostheses Osseointegration in Clinical Dentistry" published by Quintessence Publishing Company 1985.

Primary Examiner—Nicholas D. Lucchesi
Attorney, Agent, or Firm—Nixon & Vanderhye

[57] ABSTRACT

An arrangement usable as a core for a dental prosthesis or as a transfer jig in forming a model of an aveolar arch with one or more implants, comprising a nut which is for fitting in a hexagonal portion of a socket in the implant, a ring for fitting over the nut and seating around the mouth of the socket, and a post for screwing through the nut and the ring to the implant. The ring also has a hexagonal bore portion which receives part of the nut. Thus, the ring is located spatially and angularly relative to the implant without being socketed therein. When a dental impression has been formed with a plurality of the rings embedded therein, or when a sub-frame for a bridge has been made up on two or more such rings on a model of the aveolar arch made from that impression, it is removed by unscrewing the post and withdrawing it and the nut. Thus, the impression or bridge sub-frame is easily removed despite the probability that the axes of the implants in the aveolar arch are not parallel.

16 Claims, 7 Drawing Sheets

METHOD OF FORMING A DENTAL PROSTHESIS FOR MOUNTING IN AN IMPLANT, A METHOD OF FORMING A DENTAL MODEL FOR USE THEREIN, A DENTAL FORMATION MOUNTING ARRANGEMENT

DESCRIPTION

This invention relates to a method of making a model of at least part of the gum and any adjacent teeth that surround one or more implants embedded in a jawbone of a patient, there being for each implant in the jawbone a similar substitute implant similarly positioned in the model; to a method of forming a dental prosthesis for mounting in an implant which is embedded in a jawbone of a patient, to a dental formation mounting arrangement and to a range of cores which each have a head on which a dental prosthesis is to be mounted and a shank which is adapted to be fitted in a standard socket formed in an implant. The dental formation may be a dental impression or a prosthesis, such as a moulded false tooth crown or bridge, which is to be fixedly mounted in either an implant which is embedded in a jawbone of a patient or in a socket formed in a core which is fixed in such an implant.

After a period, say three months, has been allowed for an implant in a jawbone of a patient to settle, it is usual for an impression to be made in plastic material of the surfaces of at least part of the gum, and any adjacent teeth, that surround the embedded implant and to be used to make a model of that part of the gum and the adjacent teeth. A dental technician uses the model to make a dental prosthesis, which may be in the form of a false tooth, for fitting into a socket in the implant.

An integrated implant prosthesis must fit accurately and be meticulously designed in order to optimise stress distribution to the supporting bone. Therefore it is essential for the prosthetic restoration of an implant that the position of each implant in a jawbone be accurately recorded and transferred to the model. This is particularly important for a screw retained prosthesis. Also, from a contribution "Prosthodontic Procedures" by George A. Zarb and Tomas Jansson in "Tissue-Integrated Prostheses—Osseointegration in Clinical Dentistry" published by Quintessence Publishing Co. Inc. in 1985, we learn that a nonparallel, fan-shaped location of implant fixtures is not conducive to optimal stress loading and that clinical experience suggests a need for parallel upright implant fixtures otherwise the fixtures may have to be removed or not used.

In practice relative orientation of the implant to the desired orientation of the dental prosthesis it is to support is unpredictable, both because the actual location of the settled implant is difficult to predict and because the dental surgeon may have to overcome one or more of a number of problems when implanting the implant which means that the orientation of the implant may differ from the optimum. Hence the desirable parallel arrangement of implants is difficult to achieve. Indeed, on occasions, it is not possible. These problems are discussed in WO88/03007.

US-A-4708654 discloses a method of forming a model for use by a dental technician as referred to above, in which each implant has a respective guiding element fitted to it by engagement of a projecting portion of the guiding element into a mating socket in the implant, the interengagement of the projecting portion and the mating socket being such as to inhibit rotation of one relative to the other, and each guiding element is attached to the respective implant by a guide pin which is inserted through a hole formed through the guiding element and screwed into the implant. An impression is taken in a dental impression tray with a window or opening in its base through which the guide pins project. On setting of the impression material, the guide pins are unscrewed from their respective implants leaving the guiding elements embedded in the set impression material. The impression tray is then removed from the patient's mouth. Dummies of the implants to which the guiding elements had been attached while the impression was formed, are fitted to the guiding elements in the impression and similarly attached thereto by guide pins, whereupon the model is formed therearound by casting so that the dummies are embedded in that model. The guide pins are then removed to enable the model to be separated from the impression.

This disclosed method has the disadvantage that it may be impossible to take an accurate impression if the implants are not parallel. Any non-parallel movement of portions of the set impression places the impression material under great stress. Less than ideal elastic recovery from deformation caused by such stress will produce deformation of the impression material and result in an inaccurate transfer of the position and orientation of the implants from the jawbone to the model and thus to inaccuracies in the latter. Also it will be difficult to remove the impression tray from the gum if the angle of an implant relative to the jawbone in which it is embedded is at great variance to the angle of the patient's natural teeth relative to that jawbone. This is because the path for withdrawal of the tray required to disengage the guiding element from the implant will conflict with the path along which the tray needs to be moved to separate it from the patient's natural teeth.

To avoid these problems WO88/03007 proposes the use of a core or transmucosal spacer member, with a post mounted thereon when installed, the post being for mounting a false tooth crown or other form of dental prosthesis and the core or spacer member being for fitting in a standard socket of a dental implant. This proposed arrangement is such that when installed, the core or spacer and the post mounted thereon constitute in effect an axially offset extension of the dental implant, the angle of the offset of the post axis being variable and selectable, and the offset extension being adjustable as to its orientation in azimuth relative to the dental implant, prior to permanent or semi-permanent fixing, by relative rotation of parts at a bonded and preferably keyed plug and socket type connection between the core or spacer member and the dental implant.

An object of this invention is to provide a method of making a model of at least part of the gum and any adjacent teeth that surround one or more implants embedded in a jawbone of a patient which avoids the problems with the known methods as discussed above.

According to one aspect of this invention there is provided a method of making a model of at least part of the gum and any adjacent teeth that surround one or more implants embedded in a jawbone of a patient, there being for each implant in the jawbone a similar substitute implant similarly positioned in the model, in which the or each implant in the jawbone has respective locating means comprising a respective locating element attached to it by respective fixing means and interengaged with it so as to be held against rotation relative to it whilst an impression of said at least part of the gum and any adjacent teeth is taken around the or each locating means, the or each fixing means being released and removed from the respective implant in the jawbone once the material of the impression has set so as to disconnect the locating means from the respective implant, the set impression with said locating means embedded therein is removed from the patient's mouth and the or each fixing means is used to fix and locate a respective substitute implant in place relative to the set impression whilst the model is formed therearound by casting, the or each fixing means being released and removed from the casting when the casting is set to allow the model to be separated from the set impression, wherein the locating means for the or each implant includes a respective locating bush and, whilst the impression is being taken, the or each locating element and respective fixing means together locate relative to the respective implant, the respective locating bush which is fitted over the locating element, and when the impression is set, the or each locating element is withdrawn relative to the set impression from its positive interengagement with the standard socket of the respective implant in the jawbone leaving the respective locating bush embedded in the set impression material, the or each locating element being used, together with the fixing means after the set impression has been removed from the patient's mouth to fix and locate the respective substitute implant in place relative to the set impression whilst the model is formed therearound by casting, the or each locating element being removed with the respective fixing means when the casting is set.

Preferably the or each locating element is held against rotation relative to the respective implant by the interengagement of mating flat surfaces formed respectively on it and on said respective implant.

It is also preferable that the or each locating element and the respective locating bush are provided with means whereby angular movement of the or each locating bush relative to the respective locating element is inhibited so that the or each locating bush is located angularly relative to the respective implant. Conveniently said angular movement inhibiting means comprise mating flat surfaces formed on the or each locating element and the respective locating bush.

At the outset, a false tooth or other dental prosthesis produced by the dental technician with the aid of the model may be inaccurate and, after a trial fitting by the dental surgeon may need to be returned to the technician for modification to enable it to be correctly located. This can happen several times which leads to the provision of such a false tooth or other form of dental prosthesis being an expensive exercise, especially if precious metals are involved.

The technician forms the false tooth or other form of dental prosthesis by moulding its body around a prefabricated core which has a shank which is adapted to seat in the standard socket formed in the implant. As a result the orientation of the core, which is dependent on the orientation of the implant since that governs the orientation of the shank, is liable to be inappropriate for the desired orientation of the false tooth body or other form of dental prosthesis to be formed on that core.

Turning again to WO88/03007 the disclosed false tooth core or transmucosal spacer member has a head which is hemispherically domed except for the mouth of a hole into which is screw threaded a stud of the post, the hole having an axis which is offset by the angle of offset of the post axis. This proposed arrangement has the disadvantage that the interface between the dental prosthesis moulded on the hemispherical head around the hole into which the post is screwed will be asymmetric so that the resultant loading on the false tooth core or transmucosal spacer member will not be evenly distributed over the surface of the head. Because of that, there is a risk that the post with the dental prosthesis mounted in it will work loose in service.

According to another aspect of this invention, in a method of forming a dental prosthesis for mounting in an implant which is embedded in a jawbone of a patient, a model of at least part of the gum and any adjacent teeth which surround the embedded implant, is formed, using an impression, with a substitute implant accurately located in the model in the place of the original embedded implant, and a selection of a core from which the dental prosthesis is to be formed is made from a range of cores which each have a shank which is adapted to seat in a socket formed in the original embedded implant whereby to support and locate the respective dental prosthesis relative to the jawbone, the angle of a head of each core of the range, relative to its shank, being different from the angle by which the head of each of the other cores of the range is oriented relative to its respective shank, the model being used by a process of trial and error, during which the shank of a core under trial is located in the standard socket of the substitute implant, to identify the angle of shank relative to the head of the core that is required for the selected core head to be oriented as required relative to the jawbone when its shank is located in the standard socket of the original embedded implant.

By arranging the heads of the cores of the range to be at different angles relative to the shank, the external surface of the head surrounding a hole therein which is to receive a post on which a dental prosthesis is mounted can be formed symmetrically about that hole so as to enable loads applied to it from the dental prosthesis in use to be evenly distributed. Conveniently the external surface portion of the head that symmetrically surrounds the mouth of the hole formed in the head tapers towards that hole to provide a frusto-conical seating surface for the dental prosthesis.

Another factor with the arrangement proposed in WO88/03007 which contributes to a dental prosthesis working loose in use is the fact that the post on which it is mounted is screwed into the hole in the transmucosal spacer member.

Conveniently, the shanks of the cores are provided with means for engagement in a corresponding portion of the standard socket of the embedded implant to inhibit angular displacement of a core relative to an implant in which its shank is socketed.

According to another aspect of this invention there is provided a dental formation mounting arrangement comprising a locating element which is adapted to be engaged in a socket formed in a dental foundation member on which the dental formation is to be mounted so as to be held against rotation relative to the dental foundation member and fixing means for fixing the locating element to the foundation member when the locating element is so engaged in the socket, wherein there is provided a locating bush which is to be fitted over the locating element when the latter is engaged in the socket and which is to carry the dental formation. The dental formation may be a dental prosthesis, such as a moulded false tooth crown or bridge, or a dental impression. The dental foundation member may be an implant which is embedded in a jawbone of a patient, or a core which is fixed in such an implant and which has such a socket formed in it.

Preferably the dental formation mounting arrangement is provided with means whereby angular movement of the bush relative to the locating element is inhibited.

The locating element is preferably provided with one flat surface which is adapted to abut a corresponding flat surface which is formed in said socket and thereby to hold said locating element against rotation relative to said dental foundation member and with another flat surface which, together with a cooperating flat surface formed within the bush comprises said means whereby angular movement of the bush relative to the locating element is inhibited, wherein said one flat surface and the other flat surface are parallel.

According to a further aspect of this invention there is provided a range of cores which each have a head on which a dental prosthesis is to be mounted and a shank which is adapted to be fitted in a standard socket formed in an implant, the angle of the head of each core of the range, relative to its shank, being different from the angle by which the head of each of the other cores of the range is oriented relative to its respective shank, either in a plane which includes the axes of the head and the shank or angularly about the axis of the shank, or both.

Each core may be provided with a locating reference surface whereby to locate the core angularly relative to a dental implant to which it is fitted.

The present invention may be used when a single implant has been planted in a jawbone of a patient, or when there is more than one such implant. In the latter case, the implants may be at the locations of adjacent teeth or they may be at spaced locations interspersed with other teeth.

A method of making a model of a patient's gum and teeth having one or more implants embedded in the jawbone, and a method of using that model to form and fit a false tooth to the or each implant in that jawbone is described now by way of example with reference to the accompanying drawings of which.

A period, which is usually of the order of 3 months is left after an implant has been implanted for it to settle in the bone before the invention is carried out. Prior to making an impression of the gum in which one or more implants have been implanted, in carrying out this invention, a dental surgeon fits a transfer jig into the standard socket of the or each implant after having uncovered the or each implant by removing the soft gum tissue that had grown over it since it was implanted.

Figures 1, 2, 3, 4, 5:
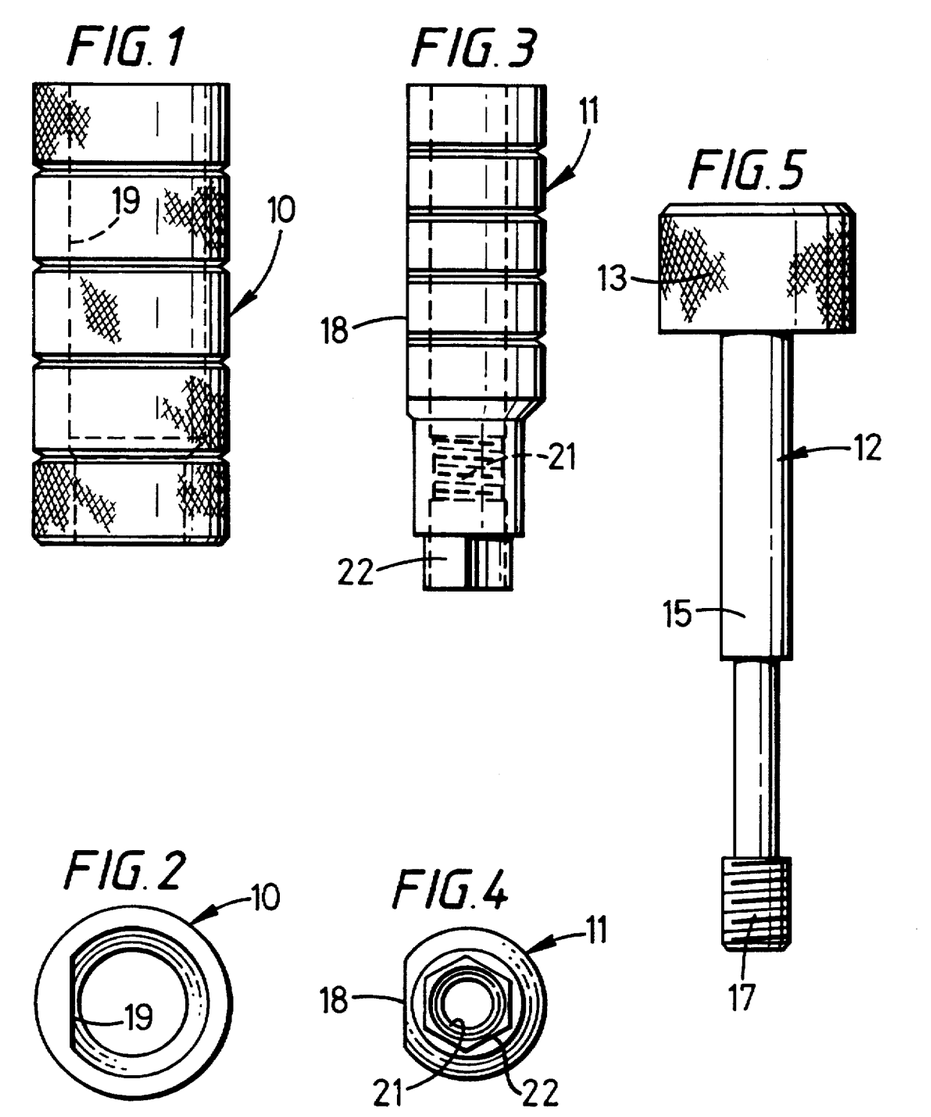
FIG. 1 is an elevation of a knurled bush of a transfer jig.
FIG. 2 is an end elevation of the knurled bush shown in FIG. 1.
FIG. 3 is an elevation of a locating sleeve component of the transfer jig.
FIG. 4 is an end elevation of the sleeve shown in FIG. 3.
FIG. 5 is an end elevation of a screw component of the transfer jig.

FIGS. 1 to 5 show the elements of such a transfer jig. They comprise an externally knurled bush 10 (FIGS. 1 and 2), a locating sleeve 11 (FIGS. 3 and 4) and a bolt 12 (FIG. 5). The bolt 12 has a head 13 which has a diameter larger than the outside diameter of the sleeve 11 and smaller than that of the bush 10, and a shank which comprises a major portion 15 which extends from the head 13 and is a sliding fit in a bore of the sleeve 11, and a screw threaded end portion 17. The sleeve 11 is a sliding fit within the bush 10. They are locked against relative angular motion by being formed with mating flats 18 and 19. A part 21 of the bore of the sleeve 11 is tapped to receive the threaded bolt end portion 17. The tapped bore part 21 is nearer to one end of the sleeve 11 than to the other. That nearer end portion of the sleeve 11 comprises a hexagonal headed portion 22. One of the flat surfaces of the hexagonal headed portion 22 is parallel to the external flat surface 18 of the sleeve 11. The bush 10 is chamfered at one end.

Figure 6:
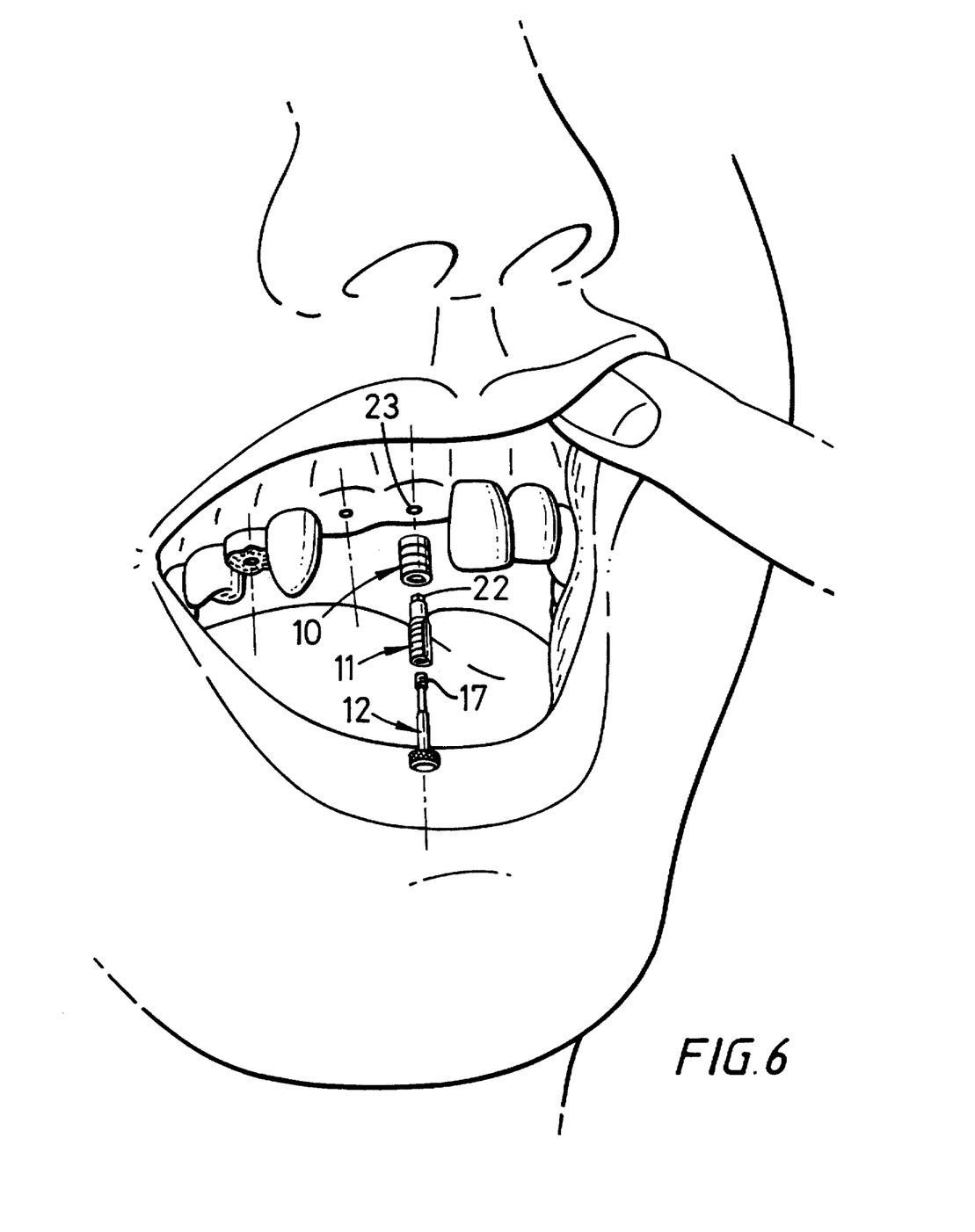
FIG. 6 is a perspective illustration of the transfer jig being fitted to an implant in the upper jawbone of a patient.
Figure 7:
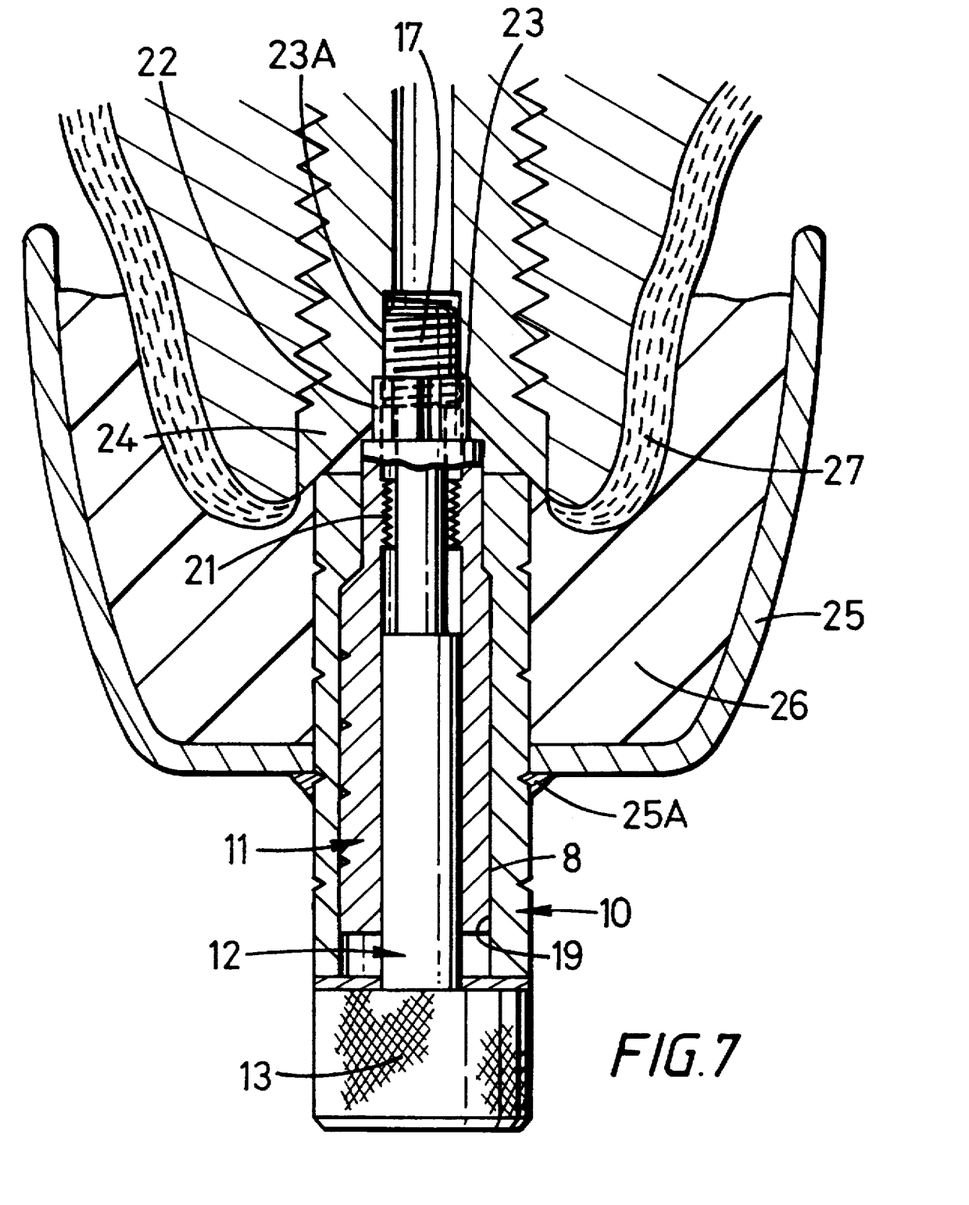
FIG. 7 is a transverse section of the transfer jig comprising the components shown in FIGS. 1 to 5 and part of the upper aveolar arch of a patient including an implant to which the transfer jig is fitted, with an impression tray fitted therearound, the section being in a plane which includes the axes of the implant and the transfer jig.

Referring to FIGS. 6 and 7, in fitting the transfer jig, the dental surgeon places the hexagonal headed portion 22 of the sleeve 11 in the hexagonal portion 23 of the standard socket of the respective implant 24 so that the sleeve 11 is located against angular motion relative to that implant 24, the sleeve 11 being within the bush 10 which has its chamfered end resting on that implant 24. The bolt 12 is then inserted through the bore of the sleeve 11 and its threaded end portion 17 is screwed through the tapped bore part 21 and into a tapped portion 23A of the standard socket of the implant 24 to locate and fit the transfer jig releaseably relative to the implant 24.

The dental surgeon then places an impression tray 25 containing plastic material 26 around the or each transfer jig to form the impression so that part of the knurled bush 10 of the or each transfer jig becomes an insert in the plastic material 25 which closely surrounds it. Part of the or each transfer jig, including part of the respective bush 10 projects through an aperture in the tray 25, to which it is bonded by a quick setting resin bonding agent 25A, so that the or each bolt head 13 is exposed.

Figure 8:
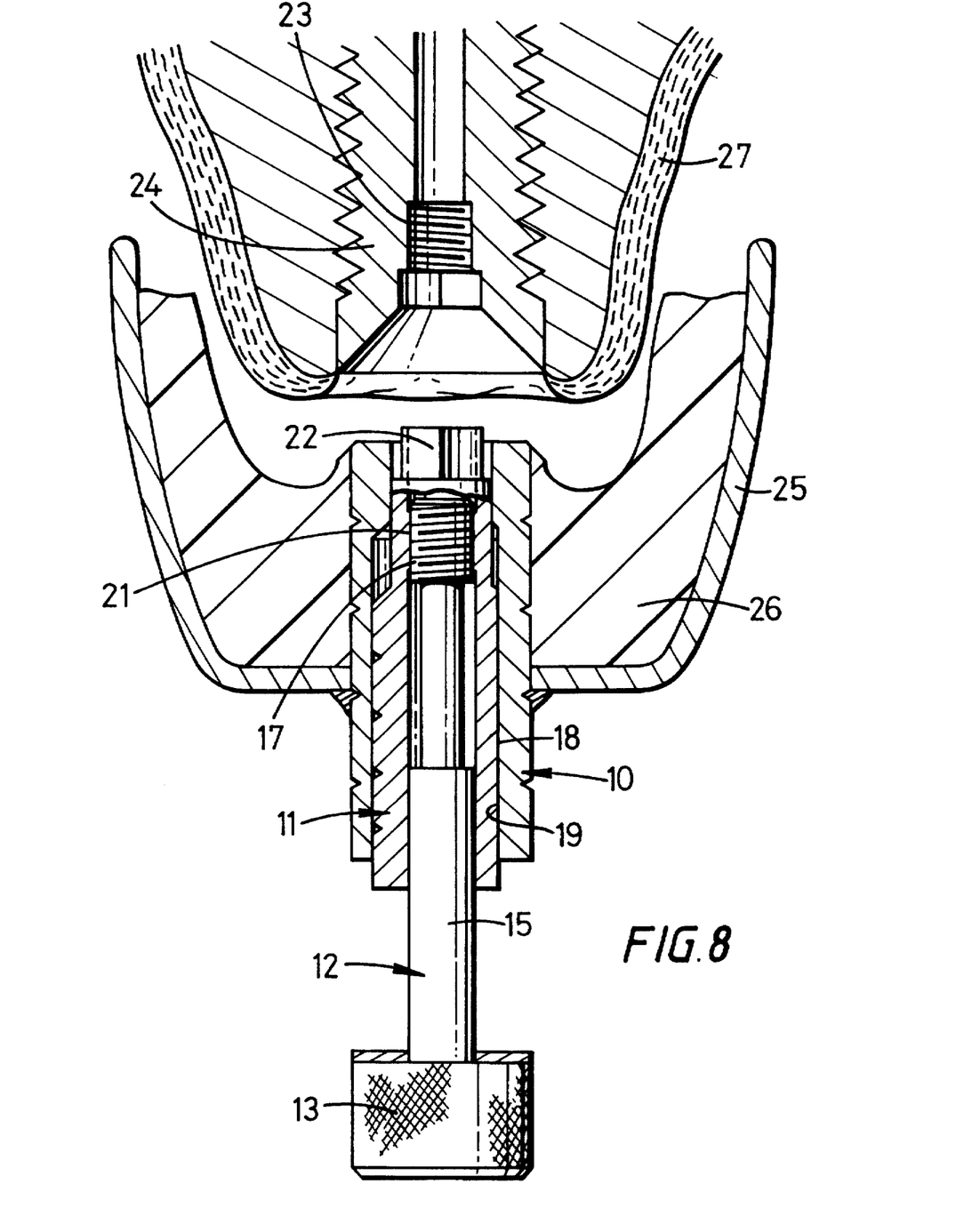
FIG. 8 is a view similar to FIG. 7 showing the transfer jig and impression separated from the aveolar arch.

When the plastic material 26 has set around the or each knurled bush 10 and the patient's gum 27 to form the impression, the dental surgeon unscrews the or each bolt 12 from the respective implant 24, and engages its threaded end portion 17 in the tapped bore part 21 of the respective sleeve 11. At least when there is more than one implant 24, or when the single implant is at an angle which is seriously at variance with the angle of the patient's natural teeth, he removes each bolt 12 and respective sleeve 11 so as to withdraw the hexagonal headed portion 22 of the or each sleeve 11 out from the respective implant 24 and thereby to disconnect the transfer jig or jigs from the or each implant 24. He then removes the plastic impression from the patient's mouth, in its tray 25 (see FIG. 8) with the or each knurled bush 10 as an insert in the plastic material 26, and carrying the respective inter-engaged sleeve 11 and bolt 12 if they have not been removed, taking care to not disturb the impression significantly in so doing, and passes it to a dental technician.

The dental technician replaces the respective sleeve 11 and bolt 12 in the bore of the or each bush 10, if they have been removed. He unscrews the or each threaded bolt end portion 17 from the respective tapped bore part 21, lets the or each bolt head 13 rest on the respective sleeve 11 and pushes the or each sleeve 11 into the respective bush 10 to ensure that the respective hexagonal headed portion 22 projects from the end of the respective bush 10 remote from the respective bolt head 13. He then screws the or each threaded bolt end portion 17 into the tapped portion of the standard socket of a respective substitute implant whereby to locate the or each substitute implant with respect to the respective sleeve 11, and thus with respect to the impression, in the same position relative thereto that was occupied by the respective implant 24 in the patient's jawbone when the impression was formed. The interengagement of the flats 18 and 19 of the or each interengaged bush 10 and sleeve 11 ensures that the flats of the hexagonal headed portion 22 are in the same position relative to the plastic impression as they were when that impression was formed in the patient's mouth. Hence the flat surfaces of the hexagonal socket of the or each substitute implant, which receives the hexagonal headed portion 22, have the same location relative to the bush 10 and the plastic impression as did the flat surfaces of the hexagonal socket portion 23 of the respective implant 24 when the plastic impression was formed in the patient's mouth. The fact that the flat external surface 18 of each sleeve 11 is parallel to one of the flat surfaces of the hexagonal headed portion 22 of the sleeve 11 leads to the sleeves 11 being interchangeable. Hence it is not vital to ensure that each sleeve 11 is replaced in the same bush 10 if it was removed when the impression was removed from the patient's mouth.

The plastic material 26 with the impression formed therein and with the or each substitute implant located therein, is then used as a mould to form the model of the patient's upper aveolar arch which has the or each substitute implant moulded therein as an insert precisely located in the model in the position occupied by the respective original implant 24 in the patient's jawbone. The or each bolt 12 is unscrewed from the respective substitute implant, once the model has been moulded whereafter the plastic material 26, the tray 25 and the components 10 to 12 of the or each transfer jig are removed.

The dental technician then selects for the or each substitute implant a suitable core which will carry a moulded false tooth crown or other form of dental prosthesis. Each core comprises a head and an integral shank which has been formed to fit into the standard socket of an implant. The selection is made from a stock of such cores. The stock comprises a range of such cores with integral shanks. The angle of the head of each core of the range relative to its integral shank is different from the angle by which the head of each of the other cores of the range is oriented relative to its respective shank, either in the plane that included the axes of the head and the integral shank, or angularly about the axis of the integral shank, or both. Each core has been machined from a solid material.

Figures 9, 10, 11, 12, 20, 21:
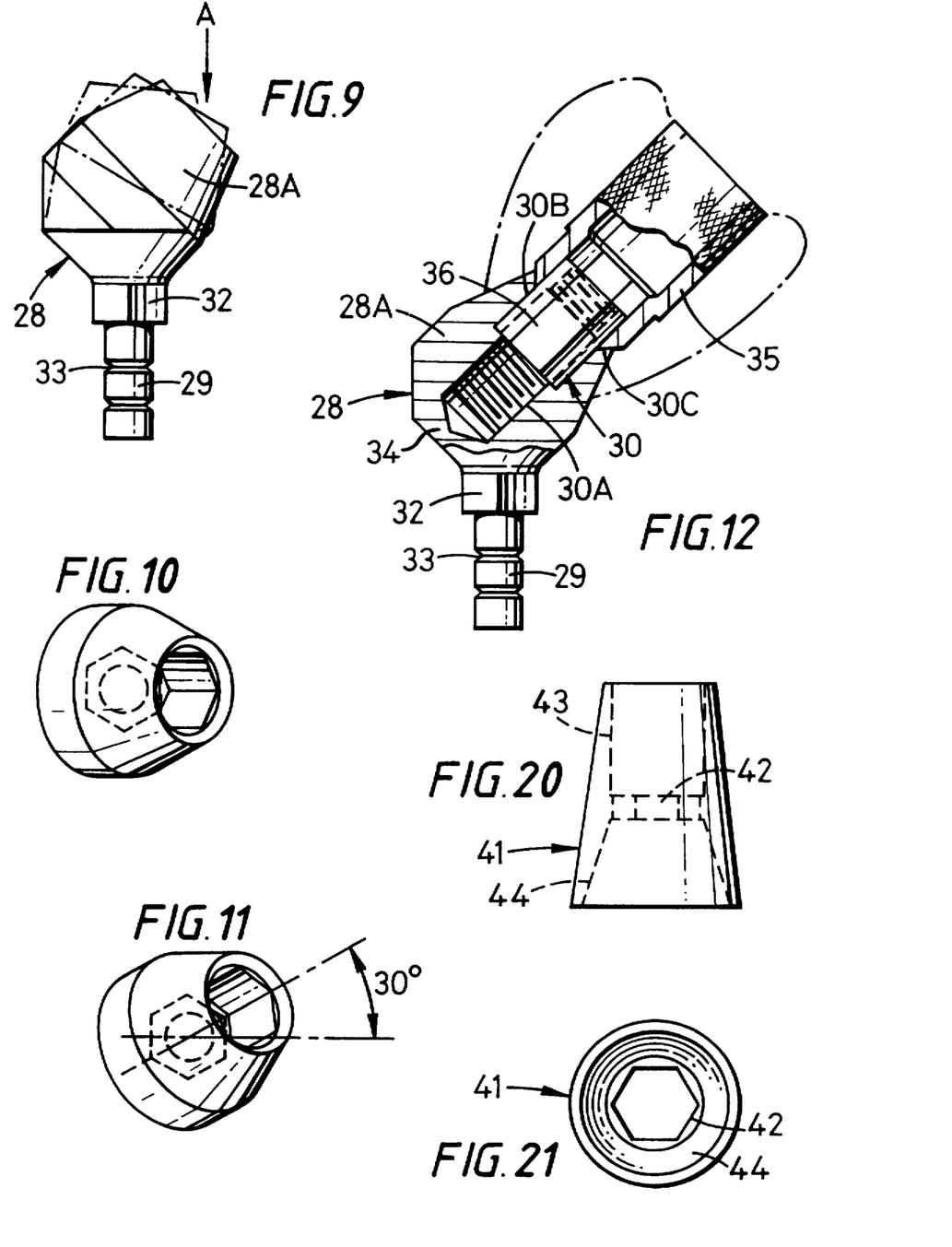
FIG. 9 is an elevation of a false tooth core with an oblique shank, similar false tooth cores with oblique shanks but having different angles included between their axes and the axis of the shank being shown chain dotted.
FIG. 10 is a view on arrow A in FIG. 9 of one variation of the core shown in FIG. 9.
FIG. 11 is a view on arrow A in FIG. 9 of another variation of the core shown in FIG. 9.
FIG. 12 is a transverse section of the false tooth core shown in full lines in FIG. 9 fitted with another form of transfer jig.
FIG. 20 is an elevation of a frusto-conical coping for fitting onto a false tooth core as shown in FIG. 9.
FIG. 21 is an end elevation of FIG. 20.

FIG. 9 shows in full lines a core 28 having a head 28A which is oblique to its standard shank 29, the angle included between their axes being 45°. It will be understood that all the other cores of the range either have the axes of their heads oblique to the axis of the respective shank as is shown chain dotted in FIG. 9, or are coaxial with the respective shank, the angles between them being within the range 0°–45°. Also, for each given included angle between 0° and 45° between the axes of the head and the shank, there is a sub-range in which the orientation of the heads differs one relative to the others angularly about the axis of the respective shank by an angle of between 0° and 30° as is explained more fully below with reference to FIGS. 10 and 11.

FIG. 12 shows each core 28 comprises a head portion 28A with a socket 30 which opens at one end and the shank 29 at an opposite end. The shank 29 has an hexagonal portion 32 where it joins the head portion 28A, its remainder being plain apart from two spaced circumferential grooves 33. The junction of the shank 29 and the head portion 28A is at the smaller diameter end of a frusto-conical portion 34 of the head portion 28A. The frusto-conical portion 34 is to seat in a counter-sunk mouth portion of a standard socket of an implant 24.

The larger diameter end of the frusto-conical portion 34 is normal to the longitudinal axis of the head when the shank and the socket are coaxial whereas, for all other cores of the range which have oblique shanks 29, the larger diameter end of the frusto-conical portion 34 is oblique to the longitudinal axis of the shank 29 as well as to the axis of the socket 30. The head portion 28A also tapers towards the mouth of the socket 30 substantially from the larger diameter end of the frusto-conical portion 34, to form a frusto-conical external surface which is symmetrical about the socket 30.

The hexagonal shank portion 32 is provided as a means for inhibiting angular movement of the core 28 relative to an implant 24 when the core 28 is fitted therein, the hexagonal shank portion 32 being sized to fit in the hexagonal socket portion 23 of the standard socket of an implant.

At one end of the sub-range in which the angular orientation of the head portions 28A of the cores 28 whose axes are oblique to the axis of the shank 29 differs from that of the others, the axis of the head portion 28A is normal to one of the flat faces of the hexagonal shank portion 32 as is shown in FIG. 10. At the other end of that sub-range the axis of the head portion 28A is at an angle of 30° to the normal to that flat face of the hexagonal shank portion 32, so that it passes through the intersection of that flat face with a juxtaposed flat face of that hexagonal shank portion 32, as is shown in FIG. 11.

That is, foundations or cores for a dental prosthesis may be provided in sets of a plurality of such cores. Each core has a head and a shank, each having an axis defining a predetermined plane. Each core also has a locating reference surface, for example, a flat surface on the hexagonal shank portion 32, which defines a fixed reference plane parallel to the flat surface and containing the axis of the shank, i.e., a plane through the axis of the shank parallel to the location reference surface, e.g., the flat face of shank comportion 32. Thus, cores in the sets of cores have different angles between the axes of the shank and head in the predetermined plane. Additionally, each core of the set of cores also has an angle between the predetermined and reference planes different from an angle between the predetermined and reference plane of each other core of the set of cores. Stated differently, the axes of the cores of a set lie at different angles one from the other in a predetermined plane and also lie at different azimuthal angles from a reference plane.

The socket 30 has a right cylindrical portion 30A at its inner end which extends over more than half its depth, it is counter-sunk at its mouth and is rebated to form a hexagonal socket portion 30B between the counter-sunk mouth portion 30C and the inner right cylindrical portion 30A which is tapped.

FIG. 12 shows an alternative form of transfer jig which is fitted to the core 28. It is shorter than the transfer jig described above with reference to FIGS. 1 to 8.

Figure 13:
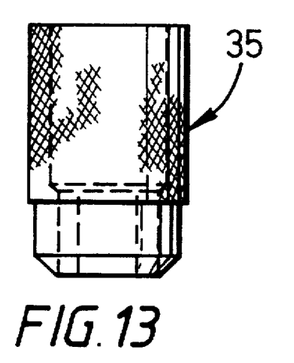
FIG. 13 is an elevation of a locking ring of the transfer jig shown in FIG. 12.
Figure 14:
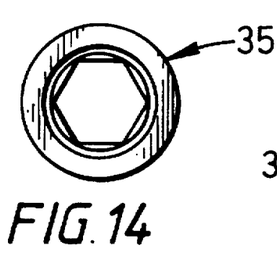
FIG. 14 is an end elevation of FIG. 13.
Figure 15:
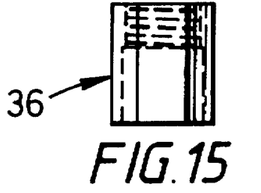
FIG. 15 is an elevation of a lock nut of the transfer jig shown in FIG. 12.
Figure 16:
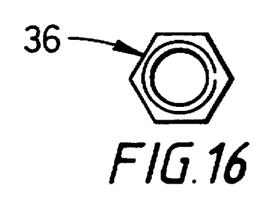
FIG. 16 is an end elevation of FIG. 15.
Figure 17:
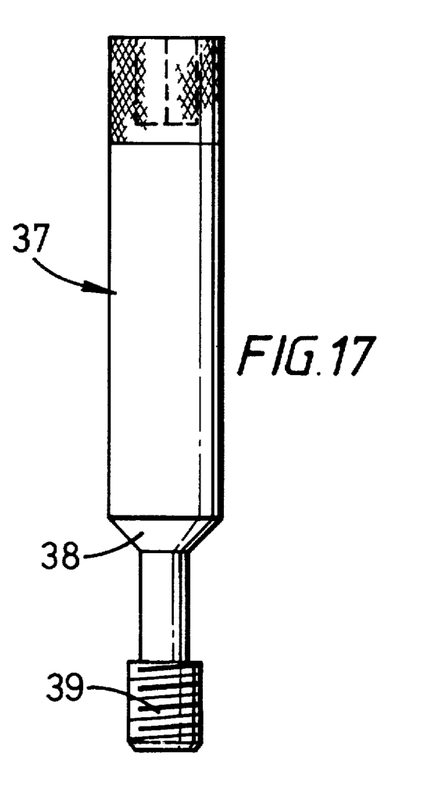
FIG. 17 is an elevation of a lock screw of the transfer jig shown in FIG. 12.

FIGS. 13 and 14 show a lock ring 35 which has a knurled outer cylindrical surface and which is chamfered at one end. It has an hexagonal internal surface. The lock ring 35 is for seating by its chamfered end in the counter-sunk mouth portion of the socket 30. FIGS. 15 and 16 show a lock nut 36 which is for spigoting into the hexagonal interior of the lock ring 35 and simultaneously into the hexagonal socket portion 30B of the socket 30 when the lock ring 35 is seated in the counter-sunk mouth portion 30C of the socket 30. The bore of the lock nut 36 is rebated from one end over a major part of its length. FIG. 17 shows a post 37 comprising a larger diameter portion, a smaller diameter shank with a frusto-conical transition portion 38 therebetween and a threaded end portion 39 at the end of the shank remote from the transition portion 38. The threaded end portion 39 is for screwing into either the nut 36 or the tapped portion 30A of the socket 30. The length of the shank is such that the frusto-conical transition portion 38 will seat upon the end of the nut 36 when the nut 36 is spigoted into the lock ring 35 and the hexagonal portion 30B of the socket 30 and when the screw threaded end portion 39 is screwed into the tapped portion 30A of the socket 30. The mating hexagonal surfaces of the nut 36, the socket portion 30B and the ring 35 restrain the transfer jig against angular movement relative to the core body portion 28.

Figure 18:
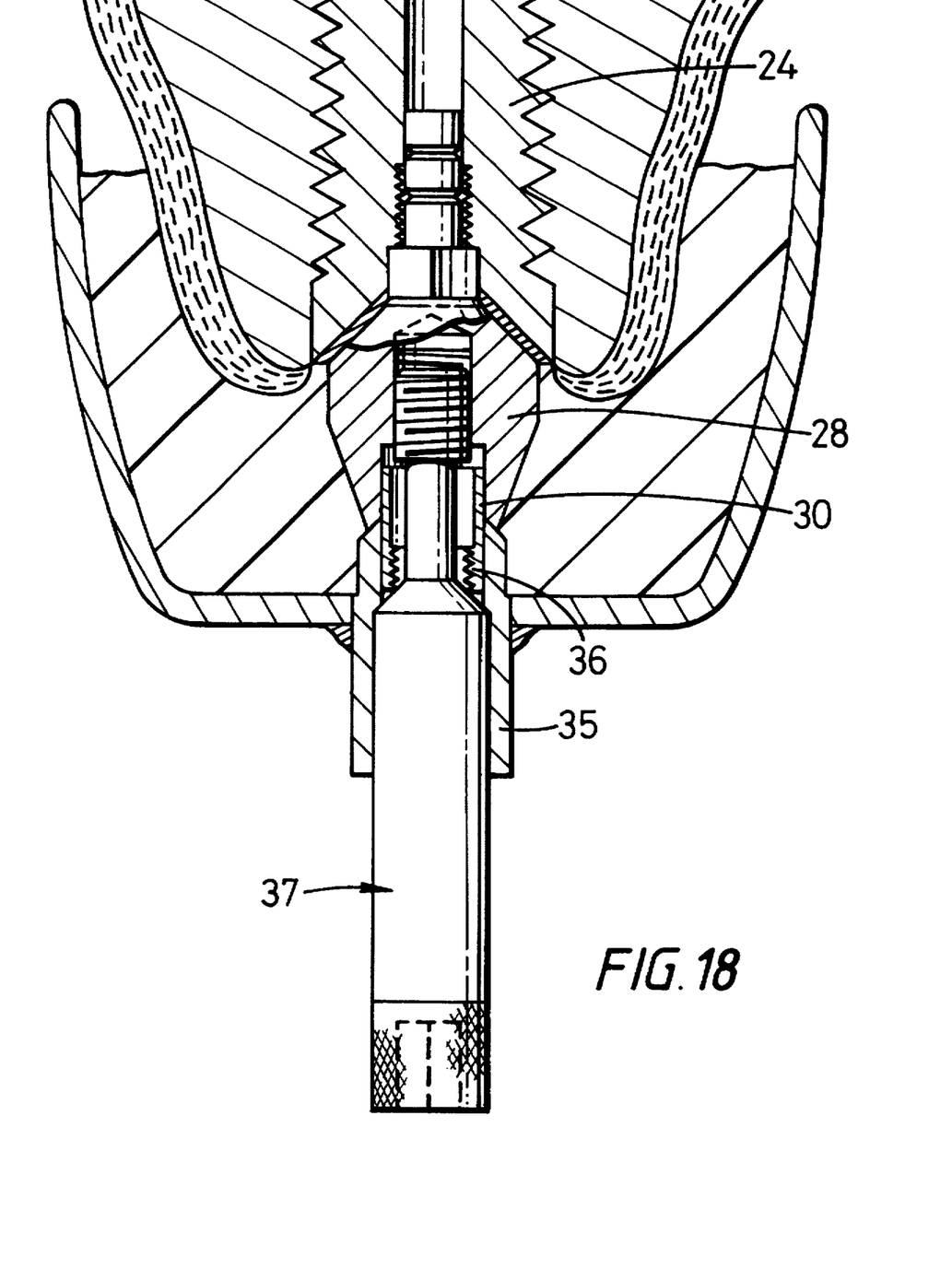
FIG. 18 is a view similar to FIG. 7 illustrating formation of an impression of a false tooth core having a coaxial shank fitted to an implant in a patient's jawbone and having the transfer jig shown in FIGS. 12 to 17 fitted to it.

FIG. 18 shows the transfer jig described above with reference to FIGS. 12–17 being used to form an impression when a core 28, which has previously been fixed to an implant 24 and used as a base of a dental prosthesis such as a false tooth, is to have another core or other dental fixture mounted in its socket 30. Details of the formation of that impression, its use to form a model and the use to which that model is to be put will be apparent to one skilled in the art from the foregoing description with reference to FIGS. 1–11. Hence they need not be described here in detail except to say that the model will be formed about a substitute core 28 rather than about a substitute implant, the post 37 having been screwed into the tapped portion 30A of the socket 30 to position the substitute core 28 relative to the impression whilst the model was moulded about it. It will be sufficient to note that the function of the lock ring 35 is equivalent to that of the locating bush 10 so that the lock ring 35 will be an insert in the resultant impression, that the function of the lock nut 36 is equivalent to that of the locating sleeve 11 and that the function of the post 37 is equivalent to that of the bolt 12. Of course the transfer jig described above with reference to FIGS. 12–17 can also be used to form such a model in which a substitute core is cast.

Having selected a core 28 from the range held in stock so as to have a core 28 of which the axis of the socket 30 will be upright when the shank 29 is fitted into the standard socket of the implant 24, that selection being made by trial and error by fitting cores 28 under trial into the socket of the substitute implant that comprises the insert in the model of the patient's gum, the dental technician forms the false tooth or other dental prosthesis on the selected core 28. The form of a false tooth moulded on the selected core is moulded by the technician in the usual way so as to match the form of adjacent teeth and adjacent portions of the gum as depicted by the model.

In forming a false tooth on the selected core 28, the dental technician may fit a post into the socket 30 of the false tooth core 28, the post having a hexagonal spigot portion which is fitted into the hexagonal portion 30B of the socket 30, the false tooth being moulded around the post and the false tooth core. Alternatively the components of the transfer jig comprising the lock ring 35, the lock nut 36 and the post 37 may be left fitted in position within the socket 30 of the false tooth core 28 and the false tooth moulded around them, as is shown by the chain-dotted line in FIG. 12. However the post 37 chosen for that purpose would be shorter than that shown in FIGS. 17–18. It would be sufficiently short that it does not project from the outer end of the lock ring 35. In another alternative, the lock nut 36, which would be formed of titanium, may be left inserted in the hexagonal socket portion 30B of the socket 30 whereas the lock ring 35 may be replaced by a similar bush formed of gold or other suitable precious metal, or of a ceramic material which in turn would be held in position by a post 37 and the false tooth formed therearound by moulding. In a further alternative, the lock nut 36 may be left in position inserted into the hexagonal socket portion 30B of the core 28 and the lock ring 35 replaced by a frusto-conical coping 41 as shown in FIGS. 20 and 21. The coping 41 is generally tubular having a hexagonal medial portion 42 of its through passage which separates a right cylindrical portion 43 of that passage from a tapered portion 44 of that passage. The right cylindrical passage portion 43 extends from the hexagonal portion 42 to the smaller diameter end of the coping 41 and the tapered portion tapers from the larger diameter end of the coping 41 to the hexagonal portion 42. The coping 41 would be seated on the frusto-conical portion of the exterior of the head portion 28A of the core 28 which tapers to the mouth of the socket 30 and would be arranged so that the lock nut 36 was spigotted into the hexagonal portion 42 of its through passage to hold it against rotation. The false tooth or other dental prosthesis would then be formed by moulding around the coping 41.

In a situation where more than one false tooth is to be made, the locking rings 35 could be linked together to form a structure to act as a sub-frame for a bridge. Such a sub-frame can be readily removed from the model of the aveolar arch on which it was made by first removing the posts 37 and the lock nuts 36 as has been described above for removing the dental impressions shown in FIGS. 7, 8 and 18.

The symmetrical arrangement of the head 28A around the axis of the socket 30, and in particular the frusto-conical external surface portion which tapers to the mouth of the socket 30 enables that tapered surface to serve as a symmetrical seat for a false tooth crown or other dental prosthesis mounted thereon. As a result loads applied to that false tooth or other dental prosthesis in use are distributed evenly over the external surface of the head portion 28A on which it is mounted. Also the symmetrical arrangement of the head portion 28A enables the hexagonal portion of the socket 30 to be formed with sufficient material around it for strength purposes.

The shorter transfer jig described above with reference to FIGS. 12 to 17 is not solely for use with a core 28 as shown in FIGS. 12 and 18. It may be fitted directly to an implant 24 in basically the same way as the larger transfer jig described above with reference to FIGS. 1 to 8. This is particularly suitable when transfer jigs are to be fitted to each of two implants 24 which have convergent axes and which are sufficiently close for the transfer jigs to interfere with one another if they are both of the larger variety as shown in FIGS. 1 to 8. In such a situation a shorter transfer jig such as is shown in FIG. 12 may be used in conjunction with one of the longer ones as shown in FIGS. 1 to 8.

Figure 19:
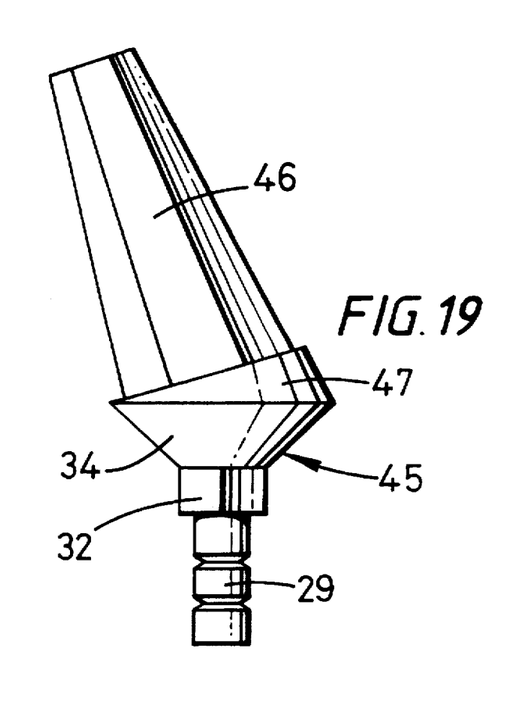
FIG. 19 is an elevation of a gauge for use in selection of a false tooth core to be fitted to an implant.

FIG. 19 shows one form of a guide pin 45. Part of the structure of the guide pin 45 is similar to a corresponding part of the structure of a core 28 as described above with reference to FIG. 9. Those similar parts, which are identified by the same reference numerals, comprise the frusto-conical portion 34, the hexagonal portion 32 and the shank 29. The remainder of the structure of the hexagonal guide pin 45 is generally oblique to the axis of the shank 29. There may be a range of such guide pins 45 having different angles included between the axis of the shank 29 and the remainder within the range 0°–45°. That remainder comprises a frusto-conical pin portion 46 which tapers to its extremity from an intermediate transition position portion 47 by which it is connected to the frusto-conical portion 34 at the larger diameter end of the latter. The diameter of the larger diameter end of the frusto-conical pin portion 46 is less than the diameter of the juxtaposed portion of the intermediate transition portion 47 so that all annular shoulder is formed by the latter around the larger diameter end of the pin 46. The hexagonal guide pin 45 is used as a means for determining angular correction when an implant is uncovered after healing several months after its initial insertion. It is also suitable for use as a gauge for selecting cores 28 from the range. It can be used to fine tune the angular orientation of an implant 24 in the jawbone when the implant 24 is being inserted. It is provided with an annular shoulder at the larger diameter end of the pin portion 46 formed by the intermediate transition portion 47 to enable it to be distinguished from sterile prosthetic components. However it could be used as the basis for a false tooth or other form of dental prosthesis, the latter being moulded around the frusto-conical pin portion.

The guide pin 45, which has a plain integral shank 29, is designed to be cemented in position in the socket of an implant when it is used as a basis for a dental prosthesis. A retrievable version of such a pin would be formed without the integral shank 29 and would be provided with a stepped through bore formed coaxially with the hexagonal portion 32. It would be fixed releaseably ill position in an implant by a locking screw which would be inserted into the through bore so that its head seats on the step and its screw portion is screwed into the tapped portion of the socket in the implant.

This invention leads to the dental technician being able to provide the dentist with a false tooth or other dental prosthesis for fitting into the implant in the patient which is more likely to be accurate and less likely to need modification for correct orientation so that provision of the false tooth should be less expensive than with know techniques. It also enables problems which arise when there are two or more implants which are not parallel for one reason or another, to be avoided.

We claim:

1. A dental formation mounting arrangement comprising a locating element for engagement in a socket formed in a dental foundation member on which the dental formation is to be mounted so as to be held against rotation relative to the dental foundation member, fixing means for fixing the locating element to the foundation member so that the locating element is engaged in the socket, and a locating bush in which the locating element is slidably fitted when the latter is engaged in the socket and which is to carry said dental formation.

2. A dental formation mounting arrangement according to claim 1 including means for inhibiting angular movement of the bush relative to the locating element is inhibited.

3. A dental formation mounting arrangement according to claim 2, wherein said bush includes a flat surface formed along an interior surface thereof, said locating element being provided with one flat surface for abutting a corresponding flat surface formed in the socket and thereby to hold said locating element against rotation relative to said dental foundation member, said locating element having another flat surface which, together with said interior flat surface of said bush, comprises said means whereby angular movement of the bush relative to the locating element is inhibited, said one flat surface and said another flat surface lying parallel to one another.

4. A dental formation according to claim 1 wherein said locating element is provided with one flat surface for abutting a corresponding flat surface formed in the socket thereby to hold said locating element against rotation relative to said dental foundation member.

5. Foundations for a dental prosthesis and connection with a dental implant comprising:

a plurality of cores;

each said core having a head on which the dental prosthesis is to be mounted and a shank for reception in a socket formed in a dental implant, said head and said shank each having an axis defining a predetermined plane;

each core having a flat location reference surface defining a fixed reference plane parallel to said surface and containing the axis of said shank;

each core of said plurality of cores having an angle between said axes in said predetermined plane different from an angle between said axes in said predetermined plane of each other another core of said plurality thereof;

at least certain of the cores of said plurality of cores having an angle between said predetermined and reference planes different from an angle between said predetermined and reference planes of other cores of said plurality thereof.

6. Foundations according to claim 5, wherein said locating reference surface locates the core angularly relative to a dental implant to which it is fitted.

7. Foundations according to claim 5, wherein the head of each core has a hole therein which is to receive a post on which a dental prosthesis is mounted and the external surface of the head surrounding the hole is formed symmetrically about that hole so as to enable loads applied to it from the dental prosthesis in use to be evenly distributed.

8. Foundations according to claim 7, wherein the external surface portion of the head that symmetrically surrounds the mouth of the hole therein tapers towards that hole to provide a frusto-conical seating surface for the dental prosthesis.

9. A foundation for a dental prosthesis comprising:

an implant for embedment in the jawbone of a dental patient and including an elongated externally threaded member having a longitudinal axial opening terminating at one end in a recess;

a dental core having a head and a shank projecting from said head for reception in and securement within said opening of said implant, said head at an end thereof distal from said shank having an opening for mounting the dental prosthesis;

a proximal end of the head adjacent a juncture of said head and said shank having a shape generally complementary to the shape of the recess at the end of the implant for disposition in said recess such that the core is substantially in fitted direct engagement with said implant;

a plurality of cores, said dental core comprising a single core selected from said plurality of cores, each core of said plurality thereof having a head and a shank with each having an axis defining a predetermined plane, each core of said plurality of cores having an angle between said axes in said predetermined plane different from an angle between said axes in said predetermined plane of another core of said plurality thereof;

each said core having a flat location reference surface defining a fixed reference plane parallel to said surface and containing the axis of said shank, at least certain of the cores of said plurality of cores having an angle between said predetermined and reference planes different from an angle between said predetermined and reference planes of other cores of said plurality thereof;

a proximal end of the head adjacent a juncture of said head and said shank having a shape generally complementary to the shape of the recess at the end of the implant for disposition in said recess such that the core is substantially in fitted direct engagement with said implant.

10. A method of making a model of at least part of a gum and any adjacent teeth that surround at least one implant embedded in a jawbone of a patient, there being for each implant in the jawbone a similar substitute implant similarly positioned in the model, comprising the steps of:

(i) providing a respective locating bush for each implant;

(ii) inserting a respective locating element into each locating bush within which it is a sliding fit;

(iii) interengaging each locating element with the respective implant so that it is held against rotation relative to that implant, thereby locating the respective locating bush relative to that implant;

(iv) attaching each said locating element to the respective implant by respective fixing means;

(v) forming an impression of settable plastic material around said gum part, adjacent teeth, each said locating element and locating bush, the latter being in abutment with the respective implant, and allowing the material to set;

(vi) disconnecting each said locating element from the respective implant by releasing and removing said fixing means from the respective implant once the material of the impression has set;

(vii) removing the set impression from the patient's mouth with each locating bush embedded therein;

(viii) using said fixing means and locating element to fix and locate a respective substitute implant in place relative to the set impression, each said locating element being inserted in the respective locating bush that is embedded in the set impression;

(ix) forming the model by casting around each said substitute implant that is fixed in place relative to the set impression; and (x) releasing and removing the fixing means from each substitute implant to allow the model to be separated from the set impression.

11. A method according to claim 10, wherein the step of interengaging includes holding each locating element against rotation relative to the respective implant by interengaging mating flat surfaces formed on the locating element and on the respective implant.

12. A method according to claim 10, including inhibiting angular movement of each locating bush relative to the respective locating element so that each locating bush is located angularly relative to the respective implant.

13. A method according to claim 12, wherein the step of inhibiting angular movement includes forming mating flat surfaces on each locating element and the respective mating bush.

14. A method of forming a dental prosthesis for mounting to an implant which is embedded in a jawbone of a patient, comprising:

(i) using an impression to form a model of at least part of the gum and any adjacent teeth which surround the embedded implant;

(ii) locating a substitute implant in the model in place of the original embedded implant; and (iii) selecting a core from which the dental prosthesis is to be formed, from a range of cores which each have a head and a shank adapted to seat in a socket formed in the original implant thereby to support and locate the respective dental prosthesis relative to the jawbone;

wherein the improvement comprises:

(iv) providing a range of cores for the step of selecting said core wherein the angle of the head of each core of the range provided is different from the angle by which the head of each of the other cores of the range is oriented relative to its respective shank;

(v) using the model by a process of trial and error which involves locating the shank of a core under trial in a standard socket of the substitute implant by directly seating the core on said substitute implant without any intervening component, to identify the angle of shank relative to the head of the core that is required for the selected core head to be oriented as required relative to the jawbone when its shank is located in the standard socket of the original embedded implant.

15. A method according to claim 14, including inhibiting angular displacement of a core relative to an implant in which its shank is socketed by providing the shanks of the cores with means for engagement in a corresponding portion of the standard socket of the embedded implant.

16. A method according to claim 14, wherein the angle of the head of each core of the range, relative to its shank, differs from the angle by which the head of each of the other cores of the range is oriented relative to its respective shank, either in a plane which includes the axes of the head and shank or angularly about the axis of the shank or both.

\* \* \* \* \*